(12) United States Patent
Suzuki et al.

(10) Patent No.: US 8,273,530 B2
(45) Date of Patent: Sep. 25, 2012

(54) METHOD FOR SIMULTANEOUS ANALYSIS OF MULTIPLE BIOLOGICAL REACTIONS OR CHANGES IN IN VIVO CONDITIONS

(75) Inventors: Miho Suzuki, Saitama (JP); Yuzuru Husimi, Saitama (JP); Yasuhiko Oki, Saitama (JP)

(73) Assignee: Miho Suzuki, Saitama-shi, Saitama (JP)

( * ) Notice: Subject to any disclaimer, the term of this patent is extended or adjusted under 35 U.S.C. 154(b) by 766 days.

(21) Appl. No.: 11/915,269

(22) PCT Filed: May 24, 2006

(86) PCT No.: PCT/JP2006/310315
§ 371 (c)(1),
(2), (4) Date: Mar. 4, 2009

(87) PCT Pub. No.: WO2006/102365
PCT Pub. Date: Sep. 28, 2006

(65) Prior Publication Data
US 2009/0117551 A1 May 7, 2009

(30) Foreign Application Priority Data
May 24, 2005 (JP) ................................ 2005-151353

(51) Int. Cl.
*C12Q 1/68* (2006.01)
*G01N 33/53* (2006.01)
*A61K 39/395* (2006.01)
*C07K 5/00* (2006.01)

(52) U.S. Cl. ........ 435/6.1; 435/6.19; 435/7.1; 536/23.1; 530/300; 424/94.1; 424/130.1

(58) Field of Classification Search .......................... None
See application file for complete search history.

(56) References Cited

U.S. PATENT DOCUMENTS

| | | | |
|---|---|---|---|
| 6,114,038 A * | 9/2000 | Castro et al. | 428/402.24 |
| 2003/0113709 A1 * | 6/2003 | Alivisatos et al. | 435/4 |
| 2005/0176029 A1 * | 8/2005 | Heller et al. | 435/6 |
| 2006/0014175 A1 * | 1/2006 | Naasani | 435/6 |

FOREIGN PATENT DOCUMENTS

| | | |
|---|---|---|
| JP | 2002-153279 | 5/2002 |
| WO | 03/003015 | 1/2003 |
| WO | 03/089663 | 10/2003 |
| WO | 2004/039830 | 5/2004 |
| WO | 2004/042404 | 5/2004 |
| WO | 2007/075910 | 7/2007 |

OTHER PUBLICATIONS

Medintz et al "Self-assembled nanoscale biosensors based on quantum dot FRET donors" Nature Materials, 2003 2: 630-638.*
Ying Wang et al., "Biological assembly of nanocircuit prototypes from protein-modified CdTe nanowires," Nano Letters, 2005, vol. 5, No. 2, pp. 243-248.
Harinder Arya et al., "Quantum dots in bio-imaging: revolution by the small," Biochemical and Biophysical Research Communications, 329 (2005), pp. 1173-1177.
Xiaohu Gao et al., "In vivo molecular and cellular imaging with quantum dots," Current Opinion in Biotechnology 2005, 16: 63-72.
Kim E. Sapsford et al., "Surface-immobilized self-assembled protein-based quantum dot nanoassemblies," Langmuir, vol. 20, No. 18, 2004, pp. 7720-7728.
Mihrimah Ozkan, "Quantum dots and other nanoparticles: what can they offer to drug discovery?" Drug Discovery Today, vol. 9, No. 24, Dec. 24, 2004, pp. 1065-1071.
Miho Suzuki et al., "Caspase-3 sensitive signaling in vivo in apoptotic HeLa cells by chemically engineered intramolecular fluorescence resonance energy transfer mutants of green fluorescent protein," Biochemical and Biophysical Research Communications, 330 (2205), pp. 454-460.
Emmanuel Chang et al., "Protease-activated quantum dot probes," Biochemical and Biophysical Research Communications, 334 (2005), pp. 1317-1321.
Soumitra S. Ghosh et al., "Real time kinetics of restriction endonuclease cleavage monitored by fluorescence resonance energy transfer," Nucleic Acids Research, 1994, vol. 22, No. 15, pp. 3155-3159.
Miho Suzuki et al., "Ryoshi dot jo ni keiko lavel shita DNA o koteika suru koto de kansatsu sareru keiko kyomei energy ido (FRET) o riyo shita DNase kassei kanjuseigata bioprobe ni tsuite," The Japan Society for Analytical Chemistry Dai 54 Nankai Koen Yoshishu, Aug. 31, 2005, p. 129 (E3005).
Jyoti K. Jaiswal et al., "Use of quantum dots for live cell imaging," Nature Methods, vol. 1, No. 1, Oct. 2004, pp. 73-78.
Igor L. Medintz et al., "Self-assembled nanoscale biosensors based on quantum dot FRET donors," Nature Materials, vol. 2, Sep. 2003, pp. 630-638.
Zhangbi Lin et al., "Studies on quantum dots synthesized in aqueous solution for biological labeling via electrostatic interaction," Analytical Biochemistry, 319 (2003), pp. 239-243.
I.L. Medintz et al., "A fluorescence resonance energy transfer-derived structure of a quantum dot-protein bioconjugate nanoassembly," PNAS, Jun. 29, 2004, vol. 101, No. 26, pp. 9612-9617.
Miho Suzuki et al., "Protease-sensitive signalling by chemically engineered intramolecular fluorescent resonance energy transfer mutants of green fluorescent protein," Biochimica et Biophysica Acta, 1679 (2004), pp. 222-229.

(Continued)

Primary Examiner — Betty Forman
(74) Attorney, Agent, or Firm — Pearne & Gordon LLP

(57) ABSTRACT

It is an object of the preset invention to provide an activity measurement molecule necessary for measuring biological reactions or changes in in vivo conditions, and a method for measuring activity using the above activity measurement molecule. It is intended to provide an activity measurement molecule used for simultaneously analyzing multiple biological reactions and/or changes in in vivo conditions, which is characterized in that one or more fluorescent molecule-labeled and/or —unlabeled biomolecules used as targets of the biological reactions or changes in in vivo conditions bind onto a quantum dot, and a method for simultaneously analyzing multiple biological reactions and/or changes in in vivo conditions using the above activity measurement molecule.

21 Claims, 7 Drawing Sheets

OTHER PUBLICATIONS

International Search Report (PCT/JP2006/310315) dated Jun. 27, 2006.

Supplementary European Search Report (EP06756521.8) dated Jun. 24, 2009.

Goldman, E.R., et al, : "Multiplexed toxin analysis using four colors of quantum dot fluororeagents," Anal. Chem. vol. 76, No. 3, Feb. 1, 2004, pp. 684-688, XP001047319.

Michalet X. et al, "Quantm dots for live cells, in vivo imaging and diagnostics." Science vol. 307, No. 5709, Jan. 28, 2005, pp. 538-544, XP001222940.

Xu, C. et al, "A self-assembled quantum dots probe for detecting beta-lactamase activity," Biochem. Biophys. Res. Commun. vol. 344, No. 3, Jun. 9, 2006, pp. 931-935, XP005404793.

* cited by examiner

Fig.5

A
MASMTGGQQMGR MSKGEELFTG VVPILVELDG DVNGHKFSVS GEGEGDATYG KLTLKFISTT GKLPVPWPTL
VTTLTYGVQC FSRYPDHMKR HDFFKSAMPE GYVQERTISF KDDGNYKTRA EVKFEGDTLV NRIELKGIDF
KEDGNILGHK LEYNYNSHNV YTTADKQKNG IKANFKTRHN IEDGSVQLAD HYQQNTPIGD GPVLLPDNHY
LSTQSALLKD PNEKRDHMVL LEFVTAAGIT *QGRGTC ELYK GG HHHHHH*

B
MASMTGGQQMGR MSKGEELFTG VVPILVELDG DVNGHKFSVS GEGEGDATYG KLTLKFISTT GKLPVPWPTL
VTTLTYGVQC FSRYPDHMKR HDFFKSAMPE GYVQERTISF KDDGNYKTRA EVKFEGDTLV NRIELKGIDF
KEDGNILGHK LEYNYNSHNV YTTADKQKNG IKANFKTRHN IEDGSVQLAD HYQQNTPIGD GPVLLPDNHY
LSTQSALLKD PNEKRDHMVL LEFVTAAG*SGIT DEVDGTC ELYK GG HHHHHH*

C
MASMTGGQQMGR MSKGEELFTG VVPILVELDG DVNGHKFSVS GEGEGDATYG KLTLKFISTT GKLPVPWPTL
VTTLTYGVQC FSRYPDHMKR HDFFKSAMPE GYVQERTISF KDDGNYKTRA EVKFEGDTLV NRIELKGIDF
KEDGNILGHK LEYNYNSHNV YTTADKQKNG IKANFKTRHN IEDGSVQLAD HYQQNTPIGD GPVLLPDNHY
LSTQSALLKD PNEKRDHMVL LEFVTAAG*SGSSGIT LEHDGTC ELYK GG HHHHHH*

D
MASMTGGQQMGR MSKGEELFTG VVPILVELDG DVNGHKFSVS GEGEGDATYG KLTLKFICTT GKLPVPWPTL
VTTLTYGVQC FSRYPDHMKR HDFFKSAMPE GYVQERTISF KDDGNYKTRA EVKFEGDTLV NRIELKGIDF
KEDGNILGHK LEYNYNSHNV YTTADKQKNG IKANFKTRHN IEDGSVQLAD HYQQNTPIGD GPVLLPDNHY
LSTQSALLKD PNEKRDHMVL LEFVTAAGIT HGMDELYK GG *RRSGTC GG HHHHHH*

E
MASSEDVIKE FMRFKVRMEG SVNGHEFEIE GEGEGRPYEG TQTAKLKVTK GGPLPFAWDI LSPQFQYGSK
VYVKHPADIP DYKKLSFPEG FKWERVMNFE DGGVVTVTQD SSLQDGEFIY KVKFIGVNFP SDGPVMQKKT
MGWEPSTERL YPRDGVLKGE IHKALKLKDG GHYLVEFKSI YMAKKPVQLP GYYYVDSKLD ITSHNEDYTI
VEQYERTEGR HHLFL SGT*DEVDGTCGG HHHHHH*

Fig.6

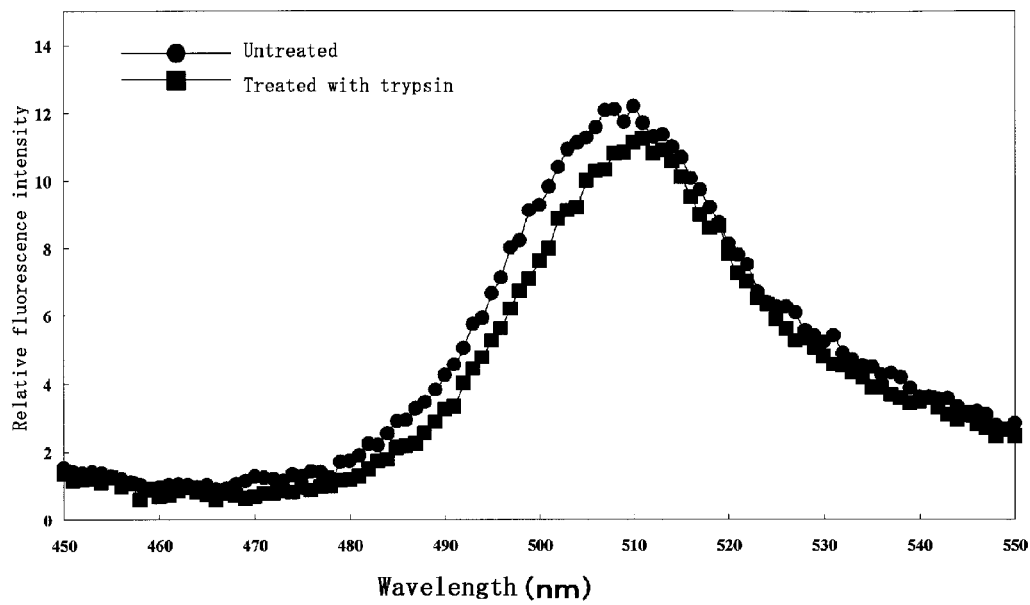

METHOD FOR SIMULTANEOUS ANALYSIS OF MULTIPLE BIOLOGICAL REACTIONS OR CHANGES IN IN VIVO CONDITIONS

TECHNICAL FIELD

The present invention relates to an activity measurement molecule necessary to measure biological reactions or dynamics in vivo, and a method to measure activity using activity measurement molecule described above. More specifically, the present invention relates to an activity measurement molecule used to measure biological reactions or dynamics in vivo conditions using a quantum dot, and a method to measure activity using the activity measurement molecule.

BACKGROUND ART

Substances existing in living organisms play various roles, and thus biological reactions also have a wide variety of patterns. The term "biological reactions" used herein means enzymatic reactions for performing degradation, transition, addition or synthesis on a protein, nucleic acid, lipid, carbohydrate or the like, and also changes in the concentrations of substances in vivo, changes in intracellular localizations, etc. Changes occurring in living organisms/cells are caused by a series of temporal or spatial chain reactions promoted by multicomponent constructs in many cases. Accordingly, by simultaneous monitoring such reactions promoted by various living organism constituents, it becomes possible to grasp the conditions of living organisms/cells more strictly. It is anticipated that information obtained as a result of such monitoring will be useful indicators in drug discovery. However, currently, neither a method of monitoring reactions of different patterns promoted by different components, nor even a method of monitoring multiple enzymatic reactions, has been developed.

The term "strictly" is used herein to mean not only a detailed analysis of changes in the conditions of organisms or cells, but also a case where internal standard reactions established must be simultaneously measured to conduct quantitative comparative discussion in diagnosis or the like, beyond differences among sample preparations, measurement apparatuses, and facilities, and where other types of reactions must be simultaneously measured as internal standard reactions even in the case of using a certain enzyme activity for the diagnosis of pathologic conditions.

A majority of products, called protein chip, are able to detect the amount (expression level) of a target protein using an antibody, just same as the ELISA method. However, a protein chip like that cannot reveal a reaction mechanism such as a detailed interaction mechanism, with which the protein is associated in a living body. In addition, even in identification of a phosphorylated protein using mass spectrometry (MS), protein chip like that is used only for confirmation of the amount of such a modified protein. That is to say, the activity of a modifying enzyme cannot be grasped using protein chip like that.

Moreover, many artificial substrates have been developed for the measurement of enzyme activity. However, it is difficult to align such artificial substrates in parallel and to use them in a high throughput manner. Since in prior art techniques, the used reagents are similar even in a case where targets to be measured are completely different, different types of activities cannot be simultaneously measured in most cases.

Hence, the present inventors have performed a protein engineering modification on GFP. Thereafter, the inventors have bound a GFP to a fluorescent dye or to a biomolecule labeled with such a fluorescent dye through introduced new amino acid sequence or the like, so as to prepare a complex molecule (bioprobe). Thus, the inventors have developed a method of monitoring various reactions promoted by living organism constituents in a parallel manner. This is a method, which comprises converting Fluorescence Resonance Energy Transfer (FRET) observed between GFP (or other types of fluorescent proteins) and a fluorescent dye (or a biomolecule labeled with such a fluorescent dye) that forms a complex with fluorescent protein in a single fusion molecule or in two closely existing molecules, into changes in states of biological reactions, and then monitoring FRET regardless within or without cells (e.g. Non-Patent Document 1, Non-Patent Document 2, and Patent Document 1). The existing protease analysis method is almost specialized in the analysis of amount. In contrast, this methodology is considered excellent one that is able to monitor reactions themselves or changes in states. Moreover, it has been revealed that such reactions or changes in states could be monitored not only by FRET but also by Fluorescence Cross-Correlation Spectroscopy (FCCS) observed between two fluorescent molecules.

Furthermore, an analysis method using FRET on a bioprobe constituted with a quantum dot and a biomolecule labeled with a fluorescent molecule has also been reported to date. However, for such a reason as difficulty in the measurement of substantial FRET and FRET dependent on a measurement target, precise measurement has not yet been achieved in the method (Patent Document 2, Non-Patent Document 3, Non-Patent Document 4, and Non-Patent Document 5).

[Patent Document 1] Japanese Patent Application Laid-Open (Kokai) No. 2002-153279

[Patent Document 2] WO2004/042404

[Non-Patent Document 1] Suzuki et al., Biochim. Biophys. Acta, 1679: 222-229, 2004

[Non-Patent Document 2] Suzuki et al., Biochim. Biophys. Res. Comm., 330: 454-460, 2005

[Non-Patent Document 3] Chang et al., Biochem. Biophys. Res. Comm., 334: 1317-1321, 2005

[Non-Patent Document 4] Lin et al., Anal. Biochem., 319: 239-243, 2003

[Non-Patent Document 5] Medintz et al., Proc. Nat. Acad. Sci. USA, 101: 9612-9617, 2004

DISCLOSURE OF THE INVENTION

Problems to be Solved by the Invention

As stated above, when multiple fluorescent proteins (for example, GFP and the color variants thereof) have been used from the viewpoint of simultaneous visualization of multiple target reactions, such fluorescent proteins have been problematic in terms of the compatibility and stability in the usage environment, and thus it has been difficult to apply such multiple fluorescent proteins to a wide range of purposes.

Moreover, in terms of the use of a quantum dot and the like, there has been a problem regard to confirmation of a generalized analysis system used for a wide range of purposes.

Furthermore, when the molecular weight of a fluorescent dye-labeled biomolecule bound to GFP is large, it would be possible to obtain a complex of the biomolecule and the GFP. However, binding efficiency is extremely poor in most cases, and thus such a complex is not suitable for practical application. Hence, it has been difficult to obtain enough amounts of measured molecules (e.g. a complex of GFP and another type of fluorescent-labeled protein, or a complex of GFP and fluorescent-labeled DNA) necessary for measuring of various biological and enzymatic reactions.

Accordingly, it is an object of the present invention to provide stably a measurement molecule, which is not influenced by the measurement environment and is used to detect multiple biological reactions or dynamics simultaneously in vivo.

In addition, it is another object of the present invention to provide a method for simultaneous analysis of multiple biological reactions using the aforementioned activity measurement molecule.

Means for Solving the Problems

Under the aforementioned circumstances, in order to measure biological reactions or dynamics in vivo, the present inventors have conducted intensive studies towards developing an activity measurement molecule, which is excellent in tolerance to the measurement environment and is used for simultaneous detection of multiple biological reactions, dynamics in vivo etc., and a measurement method. As a result, the inventors have found that the aforementioned objects can be achieved by choosing a quantum dot as an FRET donor molecule or a fluorescent molecule for FCCS, thereby completed the present invention.

At present, approximately 10 GFP color variants can be used as FRET donor molecule or a fluorescent molecule for FCCS. However, such color variants have fluorescent properties with short stoke shifts, narrow excitation spectrum and broad emission spectrum. In order to obtain multiple activity measurement molecules, it is difficult to easily acquire variants that are sufficiently distinguishable from one another on fluorescent properties. On the other hand, when compared with GFPs, there are also approximately 10 types of quantum dots, which have been confirmed to be nontoxic to living organisms. Quantum dots have fluorescent properties of a broad excitation spectrum and a narrow fluorescence spectrum. Thus, quantum dots would be superior to those of the aforementioned fluorescent proteins. Moreover, since quantum dots are inorganic molecules, they enable to produce less lot differences compared to GFP as a protein. Thus, it is considered that it becomes significantly easy to obtain quantum dots having desired fluorescent properties in the future. Furthermore, compared to GFP, quantum dots are highly tolerable to the measurement environment. Such quantum dots have light stability that is much more excellent than that of fluorescent proteins. Further, such quantum dots enable to measure fluorescence under pH conditions that greatly shifted from the area around neutral and an environment consisting of an oil layer, a high temperature, etc.

In order to monitor and analyze multiple biological reactions simultaneously, an activity measurement molecule capable of distinguishing many biological reactions and monitoring them is needed. In the case of using the conventionally used GFP as an FRET donor molecule or a fluorescent molecule for FCCS, desired fluorescence could not be obtained, unless excitation wavelengths differently dependent on individual color variants were used. However, in the case of using quantum dots, it is possible to use the same excitation wavelengths. Moreover, quantum dots having different fluorescent properties (in case that a particle size is different, emission profile is also different) can be obtained more easily than in the case of obtaining GFP or the like. Thus, the use of such quantum dots enables to increase the parallelism of a measurement target, which has been difficult to analyze simultaneously so far, and also enables to optimize the multiple simultaneous analysis method (visualization method). Furthermore, in general, a quantum dot emit longer wavelength than the case of GFP color variants such as Red fluorescent proteins. Thus, the fluorescence of such a quantum dot can be more clearly distinguished from autofluorescence observed in a living organisms.

Further, the present inventors have significantly improved difficulty in the use of a quantum dot, which has previously been reported, and they have succeeded in practical application of an analysis system using such a quantum dot. Some of the aforementioned publications regarding the prior art techniques have reported the utility of a quantum dot in the analysis of a biological reaction or the like. However, quite a lot of analysis results suggested problems and difficulty demonstrated by practical application of a quantum dot. For example, regarding detection of the activity of protease using a quantum dot, a publication (Non-Patent Document 3) reports that a quenching phenomena occurred between a quantum dot having reverse charge and a gold particle was utilized, and that a gold particle labeled with peptide was fixed on a quantum dot, quenching phenomena was then observed, and a process wherein the fluorescence of the quantum dot was recovered after the disappearance of the quenching phenomena caused by a protease action was analyzed. As a result of the analysis, ratio imaging (high-precision data obtained by narrowly-defined FRET) could not be obtained, and it also took 18 to 47 hours to measure enzymatic activity. Thus, in order to use such a quantum dot in practical analysis, considerable improvement has been required.

Considering the aforementioned respects, the invention of the present application is able to be feasible to analyze multiple reactions simultaneously and visualize thereof, which has previously been difficult.

That is to say, the present invention relates to the following (1) to (19).

(1) In a first embodiment, the present invention provides an activity measurement molecule used for simultaneous analysis of multiple biological reactions and/or dynamics in vivo, which is characterized in that one or more fluorescent molecule-labeled and/or -unlabeled biomolecules used as targets of the biological reactions or dynamics in vivo bound onto a quantum dot.

(2) In a second embodiment, the present invention provides the activity measurement molecule according to (1), which is characterized in that the above-described biomolecules are peptides and the peptides the above-described peptides bind to the above-described fluorescent molecules by a covalent or noncovalent bond.

(3) In a third embodiment, the present invention provides the activity measurement molecule according to (2), which is characterized in that the above-described covalent bond is a peptide bond.

(4) In a fourth embodiment, the present invention provides the activity measurement molecule according to any one of (1) to (3), which is characterized in that the quantum dot is coated with avidin, the above-described biomolecules are biotinylated, and the above-described biomolecules then bind to the quantum dot via a biotin-avidin bond.

(5) In a fifth embodiment, the present invention provides the activity measurement molecule according to any one of (1) to (4), which is characterized in that the number of the above-described fluorescent-labeled biomolecules is between 0 and 40, and/or the number of the above-described fluorescent-unlabeled biomolecules is between 0 and 40.

(6) In a sixth embodiment, the present invention provides the activity measurement molecule according to any one of (1) to (5), which is characterized in that the above-described biomolecules are selected from the group consisting of a nucleic acid, a protein, a peptide, an amino acid, a coenzyme, a saccharid, poly saccharide, a lipid, the derivative thereof, and the complex thereof.

(7) In a seventh embodiment, the present invention provides the activity measurement molecule according to any one of (1) to (6), which is characterized in that the above-described biological reactions are enzymatic reactions.

(8) In a eighth first embodiment, the present invention provides the activity measurement molecule according to (7), which is characterized in that the above-described enzyme is selected from the group consisting nuclease, nucleic acid-modifying enzyme, nucleic acid-synthesizing enzyme, protease, protein-modifying enzyme, poly saccharide-degrading enzyme, saccharide-nucleotide-synthesizing enzyme, and glycosyltransferase.

(9) In a ninth embodiment, the present invention provides the activity measurement molecule according to (8), which is characterized in the enzyme is nuclease and the above-described biomolecule is a nucleic acid.

(10) In a tenth embodiment, the present invention provides the activity measurement molecule according to (8), which is characterized in that the above-described enzyme is protease and the above-described enzyme is a peptide.

(11) In an eleventh embodiment, the present invention provides the activity measurement molecule according to any one of (1) to (10), which is characterized in that the above-described fluorescent molecule is selected from the group consisting of fluorescent proteins including BFP, CFP, GFP, YFP and RFP as representative examples, and the variants thereof.

(12) In a twelfth embodiment, the present invention provides a method for simultaneous analysis of multiple interactions of biomolecules, which comprises: mixing the one or more activity measurement molecules according to any one of claims 1 to 6, to which first biomolecule(s) bind, with a test sample consisting of second one or more biomolecules labeled or unlabeled with fluorescent molecule(s); incubating the mixture under conditions suitable for the interaction of the first biomolecules with the second biomolecules on quantum dots; excited each quantum dot with a wavelength suitable for the quantum dot during or after the incubation; and detecting changes in relative fluorescence intensities obtained from all the fluorescent molecules existing in the system, such as individual quantum dots, the first biomolecules bound onto the quantum dots, and/or fluorescent-labeling substances bound to the second biomolecules.

(13) In a thirteenth embodiment, the present invention provides the method according to (12) above, which is characterized in that the first biomolecule on the above-described quantum dot is selected from the group consisting of a nucleic acid, a protein, a peptide, a saccharid, poly saccharide, the derivative thereof, and the complex thereof.

(14) In a fourteenth embodiment, the present invention provides the method according to (12) or (13), which is characterized in that the above-described second biomolecule is selected from the group consisting of a nucleic acid, a protein, a peptide, a saccharid, poly saccharide, the derivative thereof, and the complex thereof.

(15) In a fifteenth embodiment, the present invention provides the method according to any one of (12) to (14), which is characterized in that the above-described test sample is a cell extract, a cell culture supernatant, blood, or body fluid.

(16) In a sixteenth embodiment, the present invention provides a method for simultaneous analysis of multiple enzymatic activities, which comprises: mixing one or more activity measurement molecules according to any one of (7) to (11) with one or more enzymes used as targets of activity detection; incubating the above-described mixture under conditions optimal to the above-described enzymes; excited each quantum dot with a wavelength suitable for the quantum dot during or after the incubation; and detecting changes in fluorescence intensities obtained from all the fluorescent molecules existing in the system, such as individual quantum dots and fluorescent labeled substances bound to individual substrates.

(17) In a seventeenth embodiment, the present invention provides the method according to (16), which is characterized in that at least one of the above-described enzymes is a protease.

(18) In a eighteenth embodiment, the present invention provides the method according to (16) or (17) above, which is characterized in that it further comprises mixing a second fluorescent-labeled substrate of the enzyme with the mixture of the activity measuring molecule.

(19) In a nineteenth embodiment, the present invention provides the method according to any one of (12) to (18), which is characterized in that the quantum dots contained in activity measurement molecules have mutually different fluorescent properties.

Advantages of the Invention

Use of the activity measurement molecule and method of the present invention enables to analyze biological reactions in an environment, in which the measurement has previously been difficult.

The activity measurement molecule (which is also referred to as a "bioprobe") of the present invention has a highly accumulated substrates within themselves. In addition, a molar extinction coefficient used for the aforementioned molecule is 10 times or more higher than that of the conventionally used fluorescent dye. Thus, the activity measurement molecule is an ultrasensitive measurement molecule, which does not require amplification of a signal or the like. The method of the present invention using such a molecule is able to provide highly sensitive results.

Use of the activity measurement molecule and method of the present invention enables to produce a protein chip capable of simultaneous measurement on multiple biological reactions or dynamics in vivo conditions, which has not previously existed. As a result, information obtained upon proteome analysis is expected to drastically increase. Also, potential to produce such a chip could contribute to progression of comprehensive analysis. Such a chip can also be used for diagnosis of disease or drug screening.

According to the activity measurement molecule and activity measurement method of the present invention, it becomes possible to allow the aforementioned activity measurement molecule to be introduced into a cell or an individual body. As a result, it becomes possible to visualize biological phenomena, which actually occurs in vivo. It is anticipated that the activity measurement molecule and method of the present invention will be available not only for the aforementioned utilization in vitro, but also for the diagnosis of disease and drug discovery, etc.

BRIEF DESCRIPTION OF THE DRAWINGS

FIG. 5 is a view showing the amino acid sequences of chimeric proteins consisting of protease recognition peptide sequences and GFP or RFP. A indicates the amino acid sequence of a recombinant protein consisting of trypsin and GFP. B indicates the amino acid sequence of a recombinant protein consisting of caspase-3 and GFP. C indicates the amino acid sequence of a recombinant protein consisting of caspase-9 and GFP. D indicates the amino acid sequence of a recombinant protein consisting of cathepsin and GFP. E indicates the amino acid sequence of a recombinant protein consisting of caspase-3 and RFP. In the figure, italics indicate the inserted sequences, and the enzyme recognition sequences are underlined.

FIG. 6 shows the results obtained by measuring trypsin activity by FRET. As a result of a trypsin treatment, the peak wavelength of fluorescence intensity shifted from 513 nm to 508 nm.

BEST MODE FOR CARRYING OUT THE INVENTION

Figure 1:
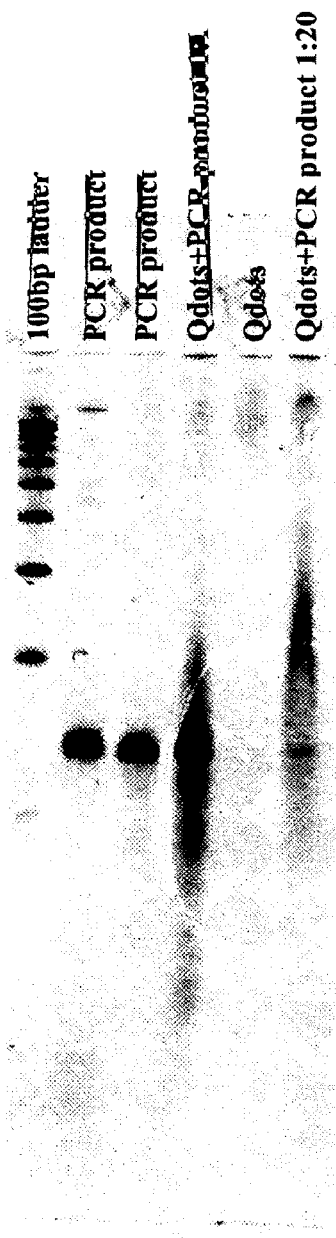
FIG. 1 shows the results obtained by subjecting substrate DNA fractions used in DNase assay (lanes 2 and 3; PCR products) and substrate DNA fractions bound to quantum dots (lanes 4 and 6; Q dots+PCR products) to polyacrylamide gel electrophoresis, and then staining the resultants with SYBR Green I (Promega Corp.). In lane 1, a 100 bp DNA marker (100 bp ladder) was electrophoresed. In lane 5 (Q dots), only quantum dots were electrophoresed.

In one embodiment, the present invention provides an activity measurement molecule used for simultaneously analyzing multiple biological reactions and/or changes in in vivo conditions, which is characterized in that one or more fluorescent molecule-labeled and/or -unlabeled biomolecules used as targets of the biological reactions or changes in in vivo conditions bind onto a quantum dot.

The term "activity measurement molecule" of the present invention is used herein to mean a biomolecule used as a target of biological reactions, changes in in vivo conditions, etc., or a binding partner (e.g. a protein, a nucleic acid, a lipid, a sugar, etc.) of the above-described biomolecule (e.g. a protein, a nucleic acid, a lipid, a sugar, etc.), which has been labeled or unlabeled with a fluorescent molecule, and which binds onto a quantum dot. Herein, a fluorescently-unlabeled biomolecule binding onto a quantum dot can be used to detect the binding pattern of the fluorescently-unlabeled biomolecule with a second biomolecule. The term "biomolecule" is used to mean all molecules that are present to play a functional or structural role in a living body. Examples of such a biomolecule include: a nucleic acid, a protein, a peptide, an amino acid, a coenzyme, a sugar, a sugar chain, a lipid, the derivative thereof, and the complex thereof (e.g. a glycoprotein, a glycolipid, etc.); various types of enzymes (e.g. nuclease, nucleic acid-modifying enzyme, nucleic acid-synthesizing enzyme, protease, protein-modifying enzyme, sugar chain-degrading enzyme, sugar nucleotide-synthesizing enzyme, and glycosyltransferase); and substrates for enzyme reactions (e.g. a protein, a nucleic acid, a lipid, a sugar, etc.).

The term "biological reaction" used herein to include all types of reactions occurring between biomolecules. For example, an enzyme reaction is a typical example of such a biological reaction. In addition, the term "changes in in vivo conditions" is used herein to include all changes in conditions such that a single biomolecule is decomposed or two biomolecules are unified by binding to each other, as a result of the interaction between such biomolecules, even in a case where no chemical reactions occur. Moreover, the changes in in vivo conditions of the present invention include not only such interaction between biomolecules, but also changes in the concentrations of biomolecules used as measurement targets (for example, a change in the concentration of related molecules occurring during a reaction, such as a change in a calcium ion concentration or a pH change that is a change in a proton concentration), changes in membrane potentials, and changes in oxidation-reduction conditions.

The term "quantum dot" is used to mean a small mass with a size of more than a dozen nm consisting of several hundreds of to several thousands of semiconductor atoms. In the 1970s, Dr. Louis Brus et al. from Bell Telephone Laboratory, U.S.A. and Dr. Alexander Efros, Alexie Ekimov, et al. from Yoffe Laboratory, the former Soviet Union, have conceived of a production method of such a quantum dot. The core technique is based on the invention described in U.S. Pat. No. 5,990,479. Even now, the technical improvement of such a production method of quantum dots has vigorously been progressing. Representative examples of such a production method include a method of cutting a two-dimensional quantum well or a one-dimensional quantum wire by electron-beam lithography and a method involving crystal growth under Stranski-Krastanov mode. In addition, a quantum dot as a finished product can also be purchased from Quantum Dot Corp., U.S.A.

When a fluorescent labeling dye (fluorescent molecule) is introduced into a biomolecule used in the active measurement molecule of the present invention, the type of the fluorescent labeling dye is not particularly limited, as long as it is able to detect fluorescence resonance energy transfer (FRET) generated between a quantum dot, or a fluctuation in two fluorescent molecules (FCCS). Examples of such a fluorescent labeling dye that can be preferably used herein include Alexa dye, BODIPY, Cy dye, and quencher, but examples are not limited thereto.

When a biomolecule used in the activity measurement molecule of the present invention is labeled with a fluorescent substance, labeling can be carried out depending on the type and properties of the biomolecule. When the biomolecule is DNA, for example, the terminus of the DNA may be labeled, or the DNA as a whole may be labeled. Such labeling can be carried out according to a method known in the present technical field. When such a biomolecule is a protein, a lipid, or a sugar, labeling can also be carried out according to a known technique.

A method for detecting FRET or the FCCS method is applied using the activity measurement molecule of the present invention, so that a biological reaction of interest or a change in a living body of interest can be detected. In this case, it is necessary that FRET be observed between a quantum dot and a fluorescent-labeled biomolecule, or that the FCCS method be able to applied. In FRET, there are required conditions such that the distance between the quantum dot and the fluorescent-labeled biomolecule is kept within a certain range. Since the quantum yield of such a quantum dot is high, the application range of FRET becomes broader than in the case of observing this phenomenon between common fluorescent dye molecules. On the other hand, in FCCS, there is no particular distance limitation. The larger the distance between the molecular weights of two molecules after the reaction, the better sensitivity that can be obtained. Since it is assumed that multiple biomolecules are immobilized on a quantum dot, the difference between the molecular weights of the two molecules can be easily realized after the reaction. Persons skilled in the art can select such conditions based on common technical knowledge.

The activity measurement molecule of the present invention can be used even in a fluidized state such as in a liquid, or even in a state where the aforementioned molecule is immobilized on a supporting medium such as a substrate. When the activity measurement molecule of the present invention is immobilized on a supporting medium, if a quantum dot is coated with avidin, the aforementioned molecule can be immobilized on a microplate, directly or via a biotin derivative. On the other hand, if a quantum dot is coated with an antibody, the aforementioned molecule can be immobilized thereon using an antibody-immobilizing column (a protein A or protein G column, etc.) or the like. Further, in both cases, a histidine-tag can be retained in a protein, and thus the activity measurement molecule of the present invention can be easily immobilized on a chip activated with $Ni^{2+}$-NTA or a gold substrate.

In production of the activity measurement molecule of the present invention, a quantum dot can be bound to a biomolecule by a method known in the present field. For such binding, a covalent bond, a noncovalent bond (for example, a coordinated bond (e.g. His tag-$Ni^{2+}$-NTA), or an antigen-antibody reaction) may be used. In addition, a biotin-avidin bond may also be used. Here is the outline. A fluorescent-labeled biomolecule (a protein, DNA, a sugar chain, etc.) is biotinylated, and it is then mixed with an avidin-coated quantum dot to form a biotin-avidin bond. Thereafter, the biomolecule can be bound onto the quantum dot via the aforementioned bond. When a biomolecule is biotinylated, if the biomolecule is a protein or the like, such binding can be achieved by allowing a biotin NHS-ester or a sulfo NHS-ester used as an amino-reactive biotinylation reagent to react with an amino acid residue or the N-terminus of a protein. That is, an amino acid residue-specific reactive biotinylation reagent can be applied to all cases. In addition, when such a biomolecule is a nucleic acid or a sugar chain, such a nucleic acid or a sugar chain is converted to an aminated derivative, and it is then allowed to react with an amino-reactive biotinylation reagent. Thus, binding can be achieved by obtaining a derivative, which corresponds to a reactive group of a biotinylation reagent.

Moreover, other than the aforementioned methods using a quantum dot coated with an antibody or avidin, a method of allowing a biomolecule to bind onto a quantum dot via a functional group (e.g. —COOH, —$NH_2$, etc.) existing on the quantum dot can also be applied. Quantum dots suitable for such methods are commercially available. Such commercially available products can also be used.

In another embodiment, the present invention provides an activity measurement molecule used for simultaneously analyzing multiple biological reactions and/or changes in in vivo conditions, which is characterized in that at least one biomolecule that is a biomolecule peptide used as a target of the biological reactions or changes in in vivo conditions and that binds to a fluorescent molecule via a covalent bond binds onto a quantum dot. The activity measurement molecule in the present embodiment can also be a useful tool for measuring a single biological reaction or the like. Any type of fluorescent molecule that has previously been known to persons skilled in the art can be used as a "fluorescent molecule" herein. For example, a fluorescent protein and the like can be used. Preferred examples include fluorescent proteins including BFP, CFP, GFP, YFP, and RFP as typical examples, and the mutants thereof. In addition, as a peptide that can be used in the present embodiment, either a peptide that functions in a living body, or a peptide portion corresponding to the functional region of a protein or the like, may be used. Moreover, such a peptide may be a portion of a protein, such as the functional domain or functional region of a certain protein. As such a peptide, any type of peptide can be used herein, as long as it is recognized by a certain biomolecule, which is expected to have an interaction with such a biomolecule, and which exerts an influence upon FRET occurring between a quantum dot and a fluorescent molecule or the like as a result of the interaction, such as a protease recognition sequence, a protein phosphorylated enzyme recognition sequence, a glycosyltransferase recognition sequence or a nucleic acid-binding sequence, or as long as it is a peptide, which exerts an influence upon FRET as a result of decomposition of the peptide.

The binding pattern of the bond between a fluorescent molecule and a biomolecule is not particularly limited. In the case of a fluorescent protein, a peptide bond is preferable for the reason that a gene engineering technique can be applied. However, covalent bonds other than such a peptide bond, such as a phosphorothioate bond, a phosphorodithioate bond, a phosphoramidothioate bond, a phosphoramidate bond, a phosphordiamidate bond, or a methylphosphonate bond, can also be used. As a noncovalent bond, a coordinated bond (e.g. His tag-$Ni^{2+}$-NTA), inclusion (a fluorescent molecule is included in the bound cyclodextrin), etc. can be used.

When a fluorescent protein is allowed to bind to a peptide via a covalent bond, it is necessary that the positional relationship between them be a positional relationship that enables observation of a great FRET change, FCCS, or the like that occurs before and after the reaction. When GFP, RFP, or a color mutant thereof is used as a fluorescent protein, for example, a peptide can be inserted into any one of the N-terminus of GFP or REP, the C-terminus thereof, and an 11-loop region that connects 11 β chains to one another. In this case, the peptide may be allowed to directly bind to the fluorescent protein or a quantum dot. In some cases, however, several amino acids (approximately 1 to 20 amino acids) acting as spacers may be inserted.

In another embodiment, the present invention provides a method, which comprises: monitoring fluorescence resonance energy transfer (FRET) occurring between a quantum dot and a fluorescent molecule-labeled biocomponent in the form of changes in the conditions of a biological reaction, using the aforementioned activity measurement molecule; or detecting fluctuation between two fluorescent molecules observed between the same above labeled biocomponent and the quantum dot by fluorescence cross-correlation spectroscopy (FCCS), so as to monitor a biological reaction such as a binding or dissociative reaction between two proteins, between a protein and a nucleic acid, between two nucleic acids or between a protein and a sugar chain, or an enzyme reaction.

FRET is detected at the highest efficiency in a state where a labeled biomolecule binds onto a quantum dot. In the case of applying the FCCS method, a fluctuation pattern is detected, in which a quantum dot and a labeled biomolecule are the same molecule. Herein, when the biomolecule contained in the activity measurement molecule is a protein, a nucleic acid, a sugar chain, or the like, if such a biomolecule is treated with protease, nuclease or sugar-chain degrading enzyme, the biomolecule is cleaved, and thus a fluorescent molecule, which has attached to the biomolecule as a labeling substance, dissociates from the quantum dot. As a result, FRET disappears, and the two fluorescent molecules act as two different molecules, so that a fluctuation pattern can be changed. During such a process, FRET, a life time of fluorescence, time-resolved fluorescence, and the like are measured using a spectrofluorophotometer, FCCS is measured using a fluorescence cross-correlation spectrometer, and such measurement results are then analyzed using each corresponding fluorescence microplate reader, so that enzyme activity can be monitored.

In addition, when such enzyme is a transferase, a non-labeled substrate is allowed to bind onto a quantum dot, and FRET generated as a result of the transfer of the second labeled substrate due to transferase is then detected. Otherwise, a change from fluorescent molecules that each differently act to a fluctuation pattern exhibiting the action as a single fluorescent molecule is measured, so as to monitor activity.

Moreover, with regard to a binding reaction between two proteins, between a protein and a nucleic acid, between nucleic acids, between a protein and a sugar chain, or the like, an activity measurement molecule is prepared by allowing a biomolecule of either one part to bind onto a quantum dot without being labeled with fluorescence, and the thus prepared activity measurement molecule is allowed to come into contact with a fluorescent-labeled biomolecule acting as a binding partner of the above activity measurement molecule.

As a result, if a FRET change from the lowest state to a higher state is detected, or if a fluctuation pattern as an independent fluorescent molecule is changed to a fluctuation pattern as two fluorescent molecules existing on a large molecule, it can be determined that the two biomolecules can bind to or interact with each other.

Since such a quantum dot is characterized in that it has a broad absorption band on a blue color side of fluorescence wavelength and exhibits a narrow fluorescence without depending on an excitation wavelength, it is possible to excite different types of quantum dots with a single wavelength so as to simultaneously obtain different types of fluorescence wavelengths. As such an excitation wavelength, it is preferable to use a wavelength that is most suitable for the properties of a quantum dot used. For example, it is better to use a wavelength at 300 to 500 nm, and preferably, a wavelength that is as far as possible from the excitation wavelengths of all acceptors existing in the activity measuring system. It is anticipated that fluorescence is exhibited at 490 nm, 525 nm, 565 nm, 585 nm, 605 nm, and 655 nm, depending on the properties of a quantum dot used.

Accordingly, even in a case where quantum dots having different fluorescent properties coexist, to which biomolecules used for measuring different biological reactions or changes in in vivo conditions have been allowed to bind, all the quantum dots having different fluorescent properties can be excited with a single wavelength, and multiple biological reactions can thereby be simultaneously monitored. For example, fluorescent-labeled DNA is allowed to bind to quantum dot 1, another fluorescent-labeled protein is allowed to bind to quantum dot 2, and a non-fluorescent-labeled sugar chain is allowed to bind to quantum dot 3. Under such conditions, an activity measurement molecule is prepared. Thereafter, a test sample that contains deoxyribonuclease, protease, glycosyltransferase and a fluorescent-labeled sugar (a mixture of purified enzymes, a cell extract, a culture supernatant, etc.) is mixed with the aforementioned activity measurement molecule, and an excitation wavelength is then applied to the obtained mixture, while incubating the mixture under suitable conditions. Thereafter, a characteristic change in the obtained fluorescence wavelength is analyzed by the FRET change detection method or FCCS method, so as to confirm the enzyme activities of the aforementioned three types of enzymes. Moreover, an interaction between proteins can be detected in the mixture consisting of a quantum dot, to which a non-fluorescent-labeled protein has been allowed to bind, and a fluorescent-labeled protein. When an environment-dependent fluorescent dye, the fluorescent properties of which are changed due to the binding thereof to a biomolecule (including chelation of metal ions), is allowed to bind to a quantum dot using a suitable spacer molecule or the like, it is also possible to apply a change in the concentration of the aforementioned biomolecule to the FRET change detection method.

As stated above, the method of the present invention can be applied to the simultaneous analysis of many biological reactions or changes in in vivo conditions.

The timing for applying an excitation wavelength to a quantum dot may be either during incubation of a test substance, or after such incubation. When certain activity or a certain reaction needs to be seen in real time, an excitation wavelength is preferably applied during such incubation. When activity is confirmed at the final stage, an excitation wavelength may be applied after incubation. When the conventional fluorescent dye has been used to make an attempt to successively observe a biological reaction in real time, fluorescence photobleaching has generated in a very short time, and thus it has been extremely difficult to obtain good results. In contrast, when the method of the present invention is used, it becomes possible to retain fluorescence for a certain long period of time because the used quantum dot is a semiconductor, and it also becomes possible to real-time monitor a comparatively slow reaction.

The activity measurement molecule of the present invention can be provided in the form of a kit. The aforementioned activity measurement molecule that adopts the form of a kit can be included in a vessel or pack, together with instructions. When the activity measurement molecule of the present invention can be provided in the form of a kit, it is preferable that the kit be wrapped in a form that enables a long-term storage without losing the functions of the aforementioned activity measurement molecule.

The activity measurement molecule included in such a kit is provided in a certain type of vessel, in which constituents are able to effectively keep their activity for a long period of time, and they are not adsorbed on the vessel or are not deteriorated depending on the material of the vessel. For example, a sealed glass ampule comprises a buffer wrapped under neutral and nonreactive gas such as nitrogen gas. Such an ampule is made from glass, polycarbonate, an organic polymer such as polystyrene, ceramic, metal, or other types of commonly used materials that are suitable for retaining a reagent. Examples of such other types of suitable vessels include a simple bottle produced from a similar substance such as ampule, and a wrapping material, the internal surface of which is lined with a foil of aluminum or alloy.

Moreover, such a kit also comprises instructions for use. The instructions for the use of the kit comprising the aforementioned activity measurement molecule may be printed on a paper or another material, and/or it may also be provided in the form of an electrically or electromagnetically readable medium such as a floppy (registered trademark) disk, CD-ROM, DVD-ROM, a Zip disk, a videotape, or an audiotape. Detailed instructions may be actually included with the kit, or may be provided via an internet website, which is designated by a kit manufacturer or distributor, or the information of which is sent via an electric mail or the like.

The examples of the present invention will be described below. However, these examples are not intended to limit the scope of the present invention.

EXAMPLES

Example 1

Measurement of Activity of Deoxyribonuclease
1. Preparation of Activity Measurement Molecule
An example for measuring the activity of deoxyribonuclease will be given.

With regard to double-stranded DNA used as a substrate, a primer set consisting of 5'-AGAACCACTCCCAGCAGCAGTTACAAACTC-3' (SEQ ID NO: 1) and 5'-ACTC-CAATTGGCGATGGCCCTG-3' (SEQ ID NO: 2) was used, and a portion (approximately 150 mer) was amplified by the PCR method using a plasmid encoding a UV5casS22 tag (refer to Non-Patent Document 2) as a template. The amplified product was subjected to electrophoresis, so as to confirm a base length thereof. Specifically, dUTP Alexa (Alexa Fluor 568-5dUTP or Alexa Fluor 532-5dUTP; Molecular Probes) was added to a PCR reaction solution (wherein 0.2 mM each dATP, dCTP and dGTP, and 0.14 mM dTTP were included, and Alexa-dUTP was added to a concentration of 0.05 mM), and the PCR reaction was then carried out under reaction conditions consisting of 30 cycles of 94° C.-2 minutes, 94° C.-30 seconds, 63° C.-30 seconds, and 72° C.-30 seconds, and a final reaction of 72° C. for 7 minutes, so as to prepare Alexa dye-labeled DNA used as a substrate of DNase. Moreover, the terminus of the primer as shown in SEQ ID NO: 1 or 2 had previously been labeled with biotin, so that the aforementioned DNA could easily bind to an avidin-coated quantum dot (SC BioSciences Corp.). This binding reaction was carried out by incubating the double-stranded DNA purified after PCR and a quantum dot in an attached buffer (composition: 2% BSA in 50 mM borate, pH 8.3 with 0.05% sodium azide) at room temperature for 2 hours. Since such a quantum dot became multivalent due to avidin coating, it was possible to bind multiple substrate DNA portions thereto (FIG. 1).

2. Measurement of Activity of Decomposing DNA

Figure 2:
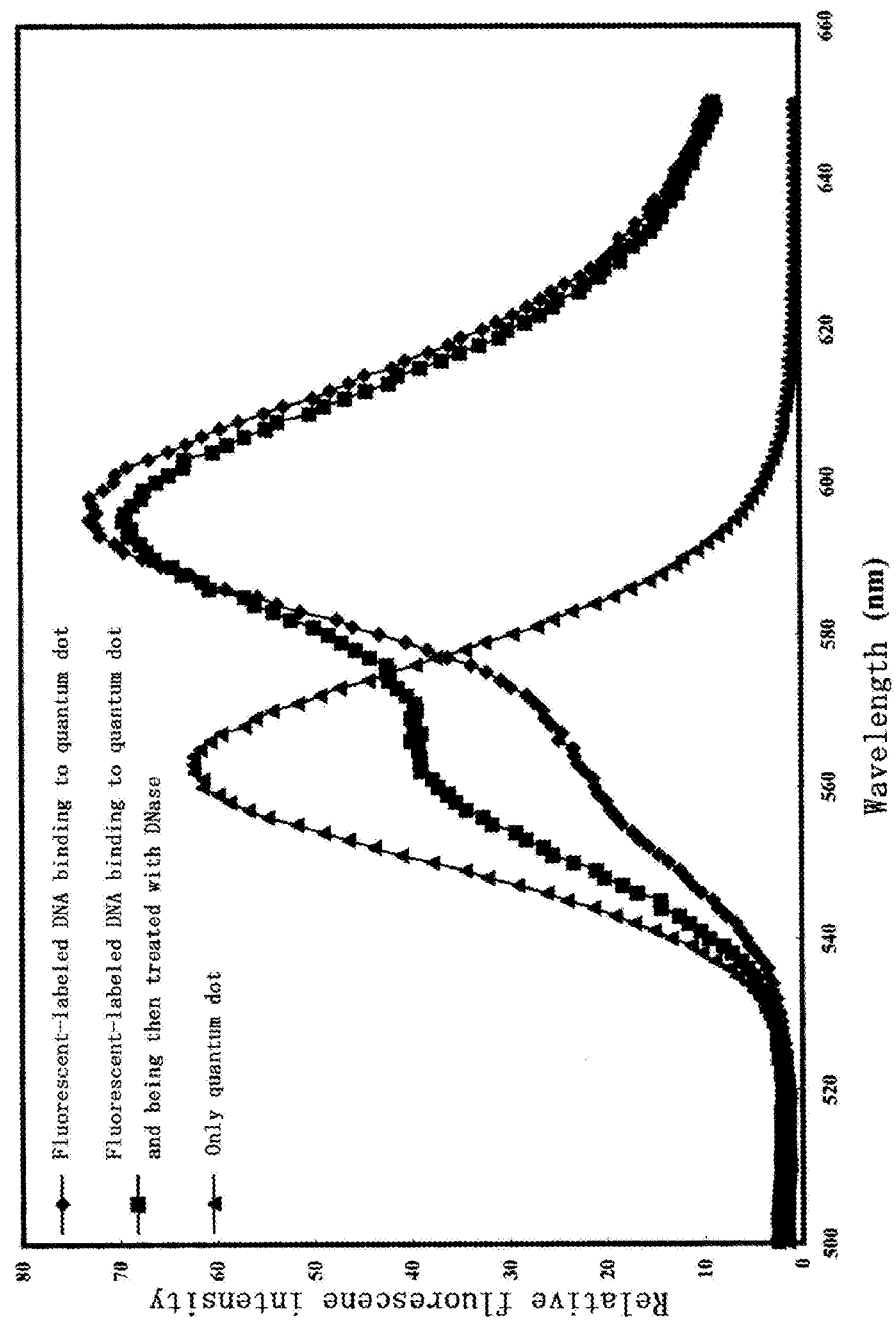
FIG. 2 shows the results obtained by measuring the FRET of only a quantum dot, a quantum dot to which a fluorescent labeled substrate DNA was allowed to bind, and a quantum dot to which a fluorescent labeled substrate DNA was allowed to bind and which was then treated with DNase.
Figure 3:
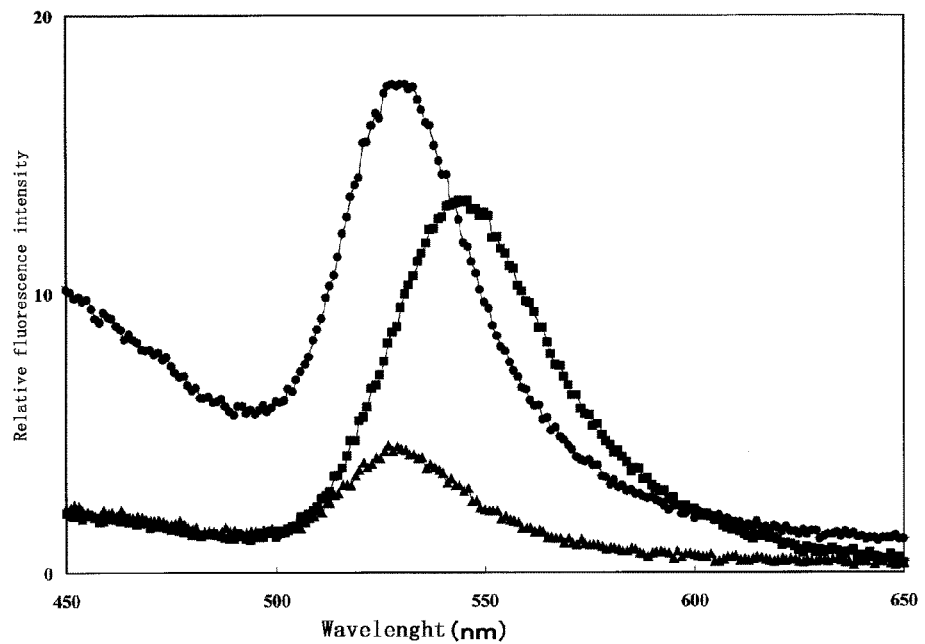
FIG. 3 shows the results obtained by measuring the FRET of a sample obtained by fixing a PCR product (labeled with dUTP-Alexa 532) on a quantum dot (QD525) and then treating it with DNase. In the case of an untreated sample (marked with filled square), FRET was still observed. However, it was then cancelled upon the DNase treatment (filled triangle). The curve marked with filled circles indicates the results obtained by treating a sample with DNase and then measuring the FRET thereof under much more sensitive conditions.

Even if a large number of substrate DNA portions (FRET acceptors) labeled with several Alexa dyes bound to a single molecule of quantum dot (FRET donor), the quantum yield of such a quantum dot was extremely high, and FRET was observed with a high efficiency (FIGS. 2 and 3). DNase (Promega) was mixed with the thus prepared activity measurement molecule, and the obtained mixture was incubated at 37° C. for 60 minutes, so as to carry out a decomposition reaction of substrate DNA. As a result, the disappearance of FRET was observed (FIGS. 2 and 3).

3. Consideration

GFP or the like was used instead of a quantum dot in the present measurement. When GFP was allowed to bind to DNA on one on one level, highly-efficient FRET was not observed if the quantities of multiple fluorescent-labeling substances incorporated into the DNA became greater than the fluorescence quantum yield of GFP (that is, it became only the fluorescence of the labeled fluorescent molecules). Thus, GFP was disadvantageous in that it could not be used as a substrate.

Furthermore, when GFP is allowed to organochemically bind to DNA via a covalent bond, almost no methods of efficiently binding a protein to a nucleic acid have been known to date. Recently, a method of efficiently binding dsDNA with a size of 150 mer or smaller to a protein has been reported. However, this method comprises complicated steps. Further, DNA with a size of approximately 150 mer is considered insufficient for the use thereof as an activity measurement probe, depending on the type of DNase to be monitored. Thus, the conventional methods have a certain limit. In contrast, the method described in the present example comprises only simple steps, and further, it is considered promptly applicable to a longer chain.

Example 2

Measurement of DNA Polymerase Activity
1. Preparation of Activity Measurement Molecule
An activity measurement molecule was prepared by immobilizing ssDNA (single-stranded DNA), with which a primer had previously been allowed to hybridize, onto a quantum dot (QD525).

2. Measurement of Activity of Decomposing DNA

Figure 4:
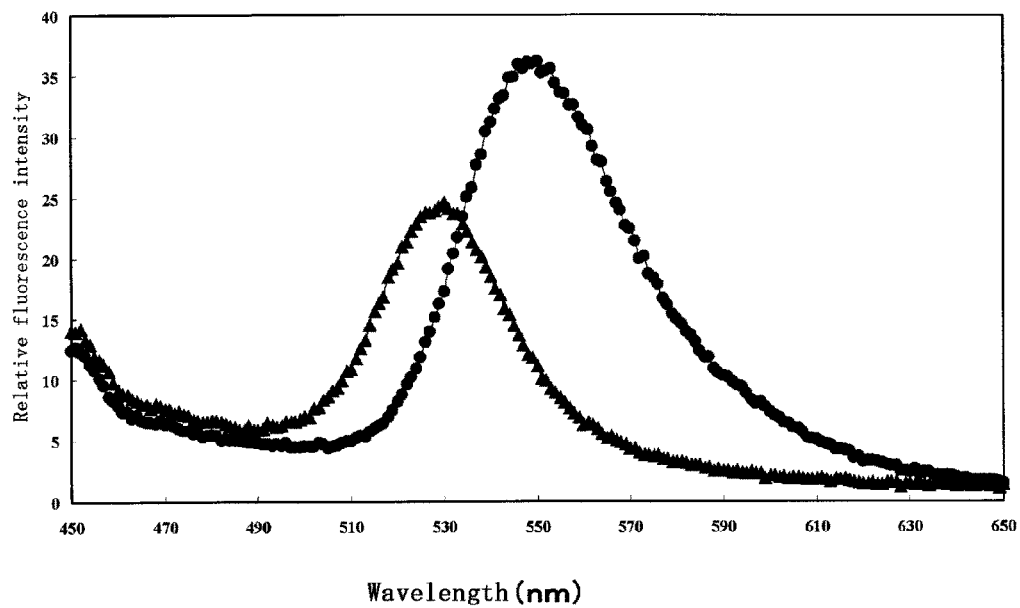
FIG. 4 shows the results obtained by fixing ssDNA (single-stranded DNA) on QD525 (wherein primers have previously been hybridized), treating the resultant with a Klenow fragment, and then observing the FRET thereof. The curve marked with filled triangles indicates the observation results of a sample that has not been treated with the Klenow fragment, and the curve marked with filled circles indicates the observation results of a sample treated with the Klenow fragment.

A Klenow fragment was added as a DNA polymerase to the prepared active molecule, so as to carry out a DNA strand elongation reaction. As a result, FRET was not observed before the treatment with DNA polymerase (the lowest state), but FRET was observed as a result of the treatment with DNA polymerase (the highest state) (FIG. 4).

Example 3

Measurement of Trypsin Activity

1. Labeling of Trypsin-sensitive Portion with GFP and Preparation of Activity Measurement Molecule In the present example, a peptide comprising a trypsin-sensitive portion was used as a biomolecule, and the activity of trypsin was measured.

As shown in FIG. 5A, a peptide (SEQ ID NO: 3) comprising a trypsin-sensitive portion was inserted into the C-terminal region of GFP, and a His tag was further added besides the above portion on the C-terminal side, so as to construct an expression vector for a GEP-trypsin recognition peptide inserted modified protein. As described in Non-Patent Document 1, this expression vector was constructed by incorporating a GFPUV5 sequence into pET21a (NOVAGEN) according to PCR, and further inserting a DNA fragment encoding the amino acid sequence as shown in SEQ ID NO: 4 into the C-terminal region thereof. Using the thus constructed expression vector, a GEP-trypsin recognition recombinant protein was allowed to express. Thereafter, using a His tag, a recognition peptide inserted recombinant protein was purified.

An amine-treated quantum dot (Amine Evitag Lake Placid Blue; Evident Technologie) and a homodivalent crosslinking reagent that was reactive with an amine group were incubated (in a 0.1 µM carbonate buffer). Thereafter, unreacted homodivalent crosslinking regent portion was eliminated using an ultrafiltration spin column. The obtained quantum dot and a Ni-NTA amine derivative were further incubated (in a 0.1 µM carbonate buffer). Thereafter, an unreacted Ni-NTA amine derivative portion was eliminated from the quantum dot to which Ni-NTA had bound, using an ultrafiltration spin column, and buffer substitution was carried out (a phosphate buffer). Thereafter, the resultant quantum dot was incubated with the purified recognition peptide-inserted recombinant protein. As a result, the recognition peptide-inserted recombinant protein could be immobilized on the quantum dot via a His tag portion.

2. Measurement of Trypsin Activity

Trypsin was added to the activity measurement molecule as prepared above, and the obtained mixture was then incubated at 37° C. for 120 minutes. As a result, the disappearance of FRET was observed (FIG. 6). That is to say, as a result of the treatment with trypsin, the peak wavelength of fluorescence intensity shifted from 513 nm (untreated with trypsin) to 508 nm (treated with trypsin).

Conventionally, in order to measure the activity of protease using a quantum dot, a long period of time (47 hours at maximum) has been required for incubation of the enzyme with a substrate. Thus, it was unlikely that the results reflected the true enzyme activity. In contrast, in the present example, by adopting the structure of the present invention, clear measurement results could be obtained as a result of incubation that was carried out for a reasonable period of time.

Example 4

Measurement of Activity of Caspase-3

1. Labeling of Caspase-3-Sensitive Portion with GFP and Preparation of Activity Measurement Molecule In the present example, a peptide comprising caspase-3 was used as a biomolecule, and the activity of trypsin was measured.

As shown in FIG. 5B, a peptide (SEQ ID NO: 5) comprising a caspase-3-sensitive portion was inserted into the C-terminal region of GFP, and a His tag was further added besides the above portion on the C-terminal side, so as to construct an expression vector for a GEP-caspase-3 recognition peptide inserted modified protein. This expression vector was constructed in the same manner as in the case of the aforementioned measurement of trypsin activity.

2. Measurement of Caspase-3 Activity

Figure 7:
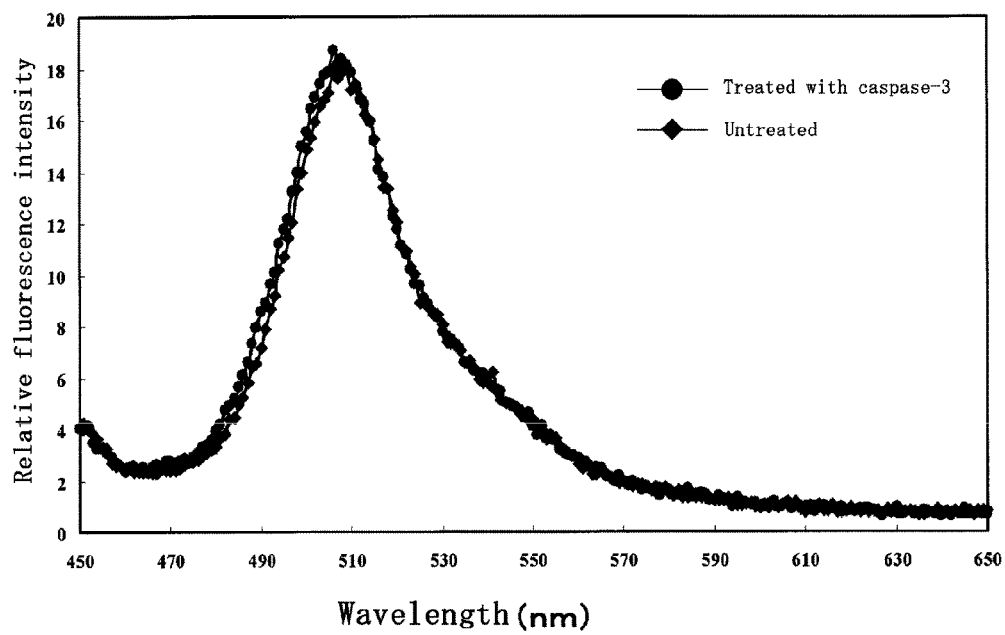
FIG. 7 shows the results obtained by measuring caspase-3 activity by FRET. As a result of a trypsin treatment, the peak wavelength of fluorescence intensity shifted from 510 nm to 506 nm.

Caspase-3 (Medical & Biological Laboratories) was added to the activity measurement molecule as prepared above, and the obtained mixture was then incubated at 30° C. for 120 minutes. As a result, the disappearance of FRET was observed (FIG. 7).

Conventionally, in order to measure the activity of protease using a quantum dot, a long period of time (47 hours at maximum) has been required for incubation of the enzyme with a substrate. Thus, it was unlikely that the results reflected the true enzyme activity. In contrast, in the present example, by adopting the structure of the present invention, clear measurement results could be obtained as a result of incubation that was carried out for a reasonable period of time. That is to say, as a result of the treatment with caspase-3, the peak wavelength of fluorescence intensity shifted from 510 nm (untreated with trypsin) to 506 nm (treated with trypsin).

It is to be noted that caspase-9 (the amino acid sequence of the GEP-caspase-9 recognition peptide inserted modified protein used in the experiment is as shown in FIG. 5C) and cathepsin E (the amino acid sequence of the GEP-cathepsin E recognition peptide inserted modified protein used in the experiment is as shown in FIG. 5D) can also be used.

Moreover, in both of the aforementioned examples using trypsin and caspase-3, GFP was used. In the case of using RFP, however, almost the same results were obtained. Furthermore, in the case of disposing such an enzyme recognition peptide on the N-terminal side of GFP or RFP as well, the same results were obtained.

Example 5

Measurement of pH Change

Figure 8:
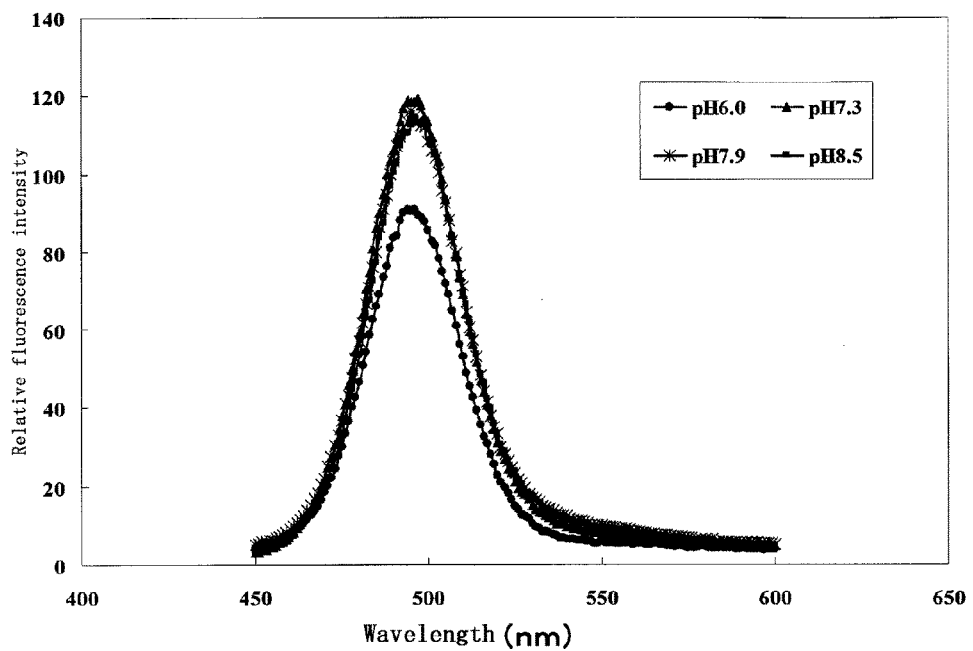
FIG. 8 shows the results obtained by exposing only quantum dots (QD) to various pH environments and observing their fluorescence spectra. Almost no changes were observed at pH 7 or greater.
Figure 9:
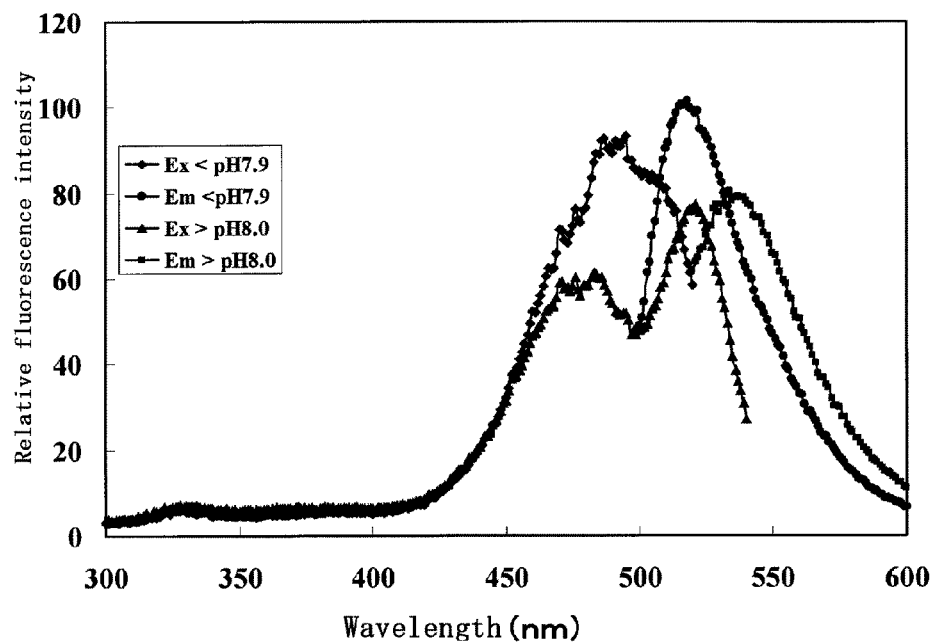
FIG. 9 shows the results obtained by exposing only pH-sensitive fluorescent dyes to various pH environments and observing their fluorescence spectra. Great changes came out around pH 7.9. However, almost no changes were observed at a pH of greater than 7.9 and at a pH of smaller than pH 7.9. The term "Ex" indicates an excitation fluorescence spectrum, and the term "Em" indicates a fluorescence spectrum obtained by the maximum excitation wavelength.
Figure 10:
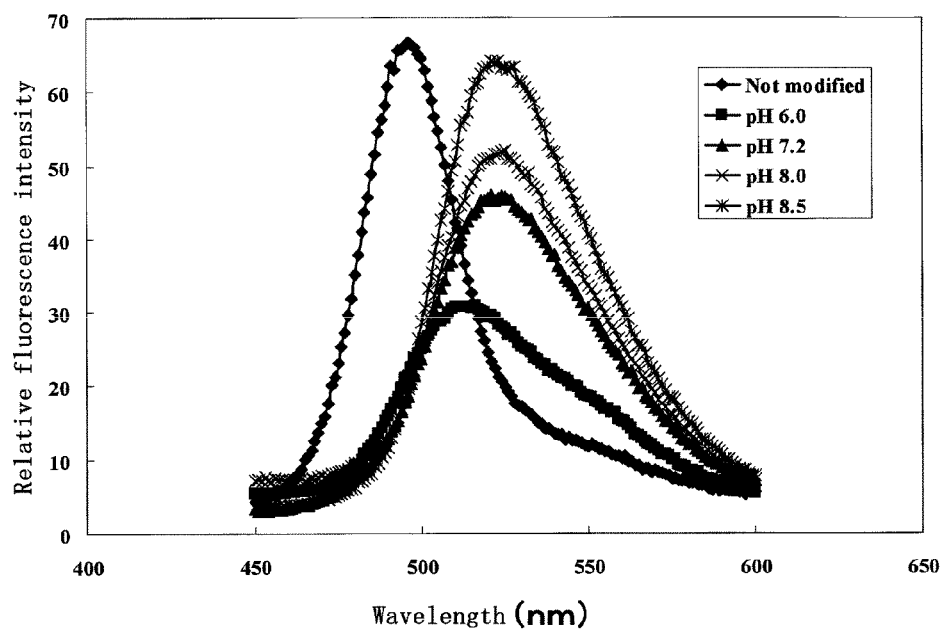
FIG. 10 shows the results obtained by immobilizing pH-sensitive fluorescent dyes on quantum dots, then exposing such quantum dots to various pH environments, and then observing their fluorescence spectra. Each spectrum had a waveform pattern that emphasized a change generated, and such a waveform pattern showed the merit of the bond. The fluorescence spectrum of only a quantum dot was used as a control, and it is shown as "Non modified" in the figure.

A Traut reagent was allowed to react with an amine-treated quantum dot (Amine Evitag Lake Placid Blue; Evident Technologies), so as to convert the amine group to a thiol group. This quantum dot and a maleimide derivative (reactive with a thiol group) of a pH-sensitive fluorescent dye (furnished from Dr. Hirokazu Komatsu, Keio University) were incubated in a phosphate buffer, so that the pH-sensitive fluorescent dye could bind onto the quantum dot. Thereafter, an unreacted pH-sensitive fluorescent dye portion was eliminated using a gel filtration column. The thus obtained pH-sensitive fluorescent dye-bound quantum dots were dispersed in each of buffers used in the monitoring of pH. The quantum dots were excited, and fluorescence spectra were measured. Herein, the fluorescent spectrum of a single quantum dot and that of a single pH-sensitive fluorescent dye were also measured in the pH-monitoring buffer. As a result, only in the case of immobilization onto the quantum dots, great changes in the fluorescent spectra that depended on pH were observed (FIGS. 8, 9, and 10), and thus it was demonstrated that a pH change measurement molecule could be produced.

Example 6

Simultaneous Detection of Activities of Multiple Enzymes

The present example describes the results obtained by simultaneously detecting the activity of nuclease and that of protease using the structure of the present invention.

A molecule used for measurement the activity of deoxyribonuclease was prepared by the same method as described in

Figure 11:
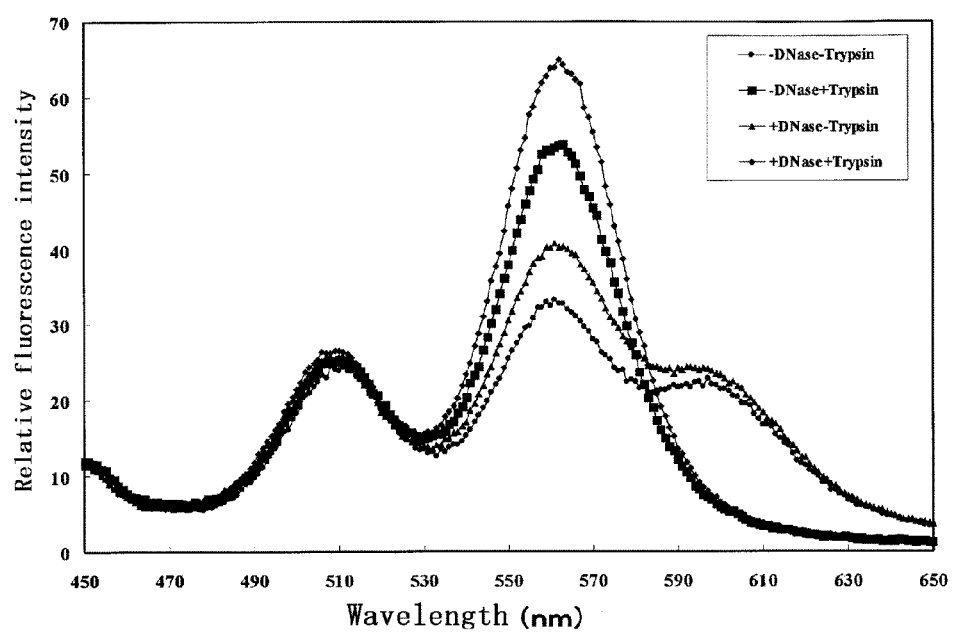
FIG. 11 shows the results obtained by simultaneously measuring deoxyribonuclease activity and protease activity. The symbols "+" and "−" show the presence or absence of each enzyme treatment.

[Example 1], using QD525 as a quantum dot and Alexa532 as a fluorescent molecule. On the other hand, a molecule used for measuring the activity of protease (trypsin was used herein) was prepared by the same method as described in [Example 2], using QD565 as a quantum dot and GFP (FIG. 5A) as a fluorescent molecule. Each of the thus prepared activity measurement molecules was dispensed into 4 tubes. A DNase-untreated and trypsin-untreated tube (FIG. 11; −DNase−Trypsin) was prepared as a control. Such a control tube, a DNase-treated and trypsin-treated tube (FIG. 11; +DNase+Trypsin), a DNase-treated and trypsin-untreated tube (FIG. 11; +DNase−Trypsin), and a DNase-untreated and trypsin-treated tube (FIG. 11; −DNase+Trypsin) were measured in terms of FRET. As a result, as shown in FIG. 11, a shift in the peak wavelength of fluorescence intensity detected by each treatment was observed in the peak wavelength of the DNase-untreated and trypsin-untreated tube. The details are as follows. In the simultaneous measurement of nuclease and protease in the present example, using the waveform pattern of −DNase−Trypsin as a base, a change in the waveform pattern in each enzyme treatment was observed, and the active status of each enzyme was monitored. Three peaks were present around 510, 560, and 600 nm. In the case of +Dnase−Trypsin, only nuclease was added. In this case, the peak around 600 nm decreased, and the peak around 560 nm increased. In the case of −DNase+Trypsin, only trypsin was added. In this case, it was observed that the peak around 510 nm shifted. In the case of +DNase+Trypsin, both enzymes were added. In this case, both of the aforementioned two changes were observed. In a case where trypsin was added and it was indicated as "+Trypsin," it was considered that an increase in the peak around 560 nm indicated the observed fluorescence wavelength of the quantum dot onto which DNA had been immobilized. In the observation method in the present example (a method of observing a change in the waveform pattern by comparing each pattern with that of the control), there were no particular problems.

From the aforementioned results, it was found that the use of the structure of the present invention enables simultaneous detection of multiple biological reactions.

The invention claimed is:

1. An activity measurement molecule comprising a biomolecule covalently bonded to a quantum dot and a fluorescent protein, wherein said biomolecule is selected from the group consisting of a nucleic acid, a protein, a peptide, an amino acid, a coenzyme, a saccharide, a poly saccharide, a lipid, derivatives thereof, and complexes thereof but excludes double stranded DNA.

2. The activity measurement molecule according to claim 1, which is characterized in that said covalent bond is a peptide bond.

3. The activity measurement molecule according to claim 1, bound to an enzyme that is selected from the group consisting of nuclease, nucleic acid-modifying enzyme, nucleic acid-synthesizing enzyme, protease, protein-modifying enzyme, poly saccharide-degrading enzyme, saccharide-nucleotide-synthesizing enzyme, and glycosyltransferase.

4. The activity measurement molecule according to claim 3, which is characterized in that said enzyme is nuclease and in that said biomolecule is a nucleic acid.

5. The activity measurement molecule according to claim 3, which is characterized in that said enzyme is protease and in that said biomolecule is a peptide.

6. The activity measurement molecule according to claim 1, which is characterized in that said fluorescent protein is selected from the group consisting of BFP, CFP, GFP, YFP and RFP, and mutants thereof.

7. A kit for simultaneously analyzing multiple enzyme activities, which comprises multiple said activity measurement molecules according to claim 1.

8. A method for analyzing enzyme activity comprising:
mixing a mixture including at least one activity measurement molecule with a test sample, wherein said activity measurement molecule comprises a biomolecule covalently bonded to a quantum dot and a fluorescent protein, wherein said biomolecule is selected from the group consisting of a nucleic acid, a protein, a peptide, an amino acid, a coenzyme, a saccharide, a poly saccharide, a lipid, derivatives thereof, and complexes thereof but excludes double stranded DNA, wherein said biomolecule is a substrate of an enzyme reaction and said test sample includes at least one enzyme used as a measurement target;

incubating the mixture under conditions in which said biomolecule reacts with said enzyme;

exciting each said quantum dot with radiation of a wavelength suitable for said quantum dot; and detecting a change in fluorescence intensity obtained from at least one of said quantum dot and said fluorescent protein as a result of said enzyme reaction to measure said activity of said enzyme.

9. The method according to claim 8, which is characterized in that said test sample is a cell extract, a cell culture supernatant, blood, or body fluid.

10. The method according to claim 8, which is characterized in that at least one activity of said enzyme is a protease reaction.

11. The method according to claim 8, which is characterized in that said mixture includes activity measurement molecules including said quantum dots that have mutually different fluorescent properties.

12. The method according to claim 8, which is characterized in that said mixture includes activity measurement molecules including said fluorescent proteins that have mutually different fluorescent properties.

13. The method according to claim 8, which is characterized in that at least one activity of said enzyme is a nuclease reaction.

14. The method according to claim 8, which is characterized in that said fluorescent protein is selected from the group consisting of BFP, CFP, GFP, YFP and RFP, and mutants thereof.

15. The method of claim 8 further comprising an other activity measurement molecule with a different quantum dot bonded to a different fluorescent molecule-labeled biomolecule, wherein said different biomolecule is a substrate of an enzyme reaction that is different from said enzyme reaction for which said biomolecule of said activity measurement molecule is said substrate, said different quantum dot having a different fluorescent property than said quantum dot of said activity measurement molecule, and at least two different enzymes in said mixture one of which said enzymes reacts with said biomolecule of said activity measurement molecule and another of which said enzymes reacts with said different biomolecule, and applying radiation of the same wavelength to said quantum dot of said activity measurement molecule and said different quantum dot to emit radiation of different wavelengths from said quantum dot of said activity measurement molecule and said different quantum dot.

16. The method according to claim 8, wherein said enzyme is selected from the group consisting of nuclease, nucleic acid-modifying enzyme, nucleic acid-synthesizing enzyme, protease, protein-modifying enzyme, poly saccharide-degrading enzyme, saccharide-nucleotide-synthesizing enzyme, and glycosyltransferase.

17. A method for analyzing enzyme activity comprising:

mixing a mixture including at least one activity measurement molecule with a test sample, wherein said activity measurement molecule comprises a biomolecule covalently bonded to a quantum dot and a fluorescent protein, wherein said biomolecule is selected from the group consisting of a nucleic acid, a protein, a peptide, an amino acid, a coenzyme, a saccharide, a poly saccharide, a lipid, derivatives thereof, and complexes thereof but excludes double stranded DNA, wherein said biomolecule is designed to have a portion that is susceptible to an enzyme reaction and said test sample includes at least one enzyme used as a measurement target;

incubating the mixture under conditions in which said enzyme reacts with said enzyme susceptible portion of said biomolecule;

exciting said quantum dot with radiation of a wavelength suitable for fluorescent emission from said quantum dot;

wherein said quantum dot is a FRET donor and said fluorescent protein is positioned in proximity to said quantum dot as a FRET acceptor such that excitement of said fluorescent protein acceptor occurs by fluorescent resonance energy transfer as said fluorescent emission from said excited quantum dot donor, and detecting a change in fluorescence intensity of said radiation emitted from at least one of said quantum dot and said fluorescent protein as a result of said enzyme reaction to measure said activity of said enzyme.

18. The method of claim 17 wherein said enzyme is selected from the group consisting of nuclease, nucleic acid-modifying enzyme, nucleic acid-synthesizing enzyme, protease, protein-modifying enzyme, poly saccharide-degrading enzyme, saccharide-nucleotide-synthesizing enzyme, and glycosyltransferase.

19. A method for analyzing enzyme activity comprising:

mixing a mixture including at least one activity measurement molecule with a test sample, wherein said activity measurement molecule comprises a biomolecule covalently bonded to a quantum dot and a fluorescent protein, wherein said biomolecule is selected from the group consisting of a nucleic acid, a protein, a peptide, an amino acid, a coenzyme, a saccharide, a poly saccharide, a lipid, derivatives thereof, and complexes thereof but excludes double stranded DNA, wherein said biomolecule is designed to have a portion that is susceptible to an enzymatic reaction, said mixture comprising at least one other activity measurement molecule with a different biomolecule covalently bonded to a different quantum dot and a different fluorescent molecule, wherein said different biomolecule is selected from the group consisting of a nucleic acid, a protein, a peptide, an amino acid, a coenzyme, a saccharide, a poly saccharide, a lipid, derivatives thereof, and complexes thereof but excludes double stranded DNA, wherein said different biomolecule is a substrate of an enzyme reaction that is different from said enzyme reaction for which said biomolecule of said activity measurement molecule is said substrate, said different quantum dot having a different fluorescent property than said quantum dot of said activity measurement molecule, and said test sample includes as measurement targets at least two different enzymes in said mixture;

incubating the mixture under conditions in which one of said enzymes reacts with said biomolecule of said activity measurement molecule and another of said enzymes reacts with said different biomolecule;

applying radiation of the same wavelength to said quantum dot of said activity measurement molecule and said different quantum dot, said radiation having a wavelength suitable for fluorescent emission from said quantum dot, said fluorescent protein, said different quantum dot and said fluorescent molecule, emitting radiation of different wavelengths from said quantum dot of said activity measurement molecule and said different quantum dot, and detecting a change in fluorescence intensity of said radiation emitted from at least one of said quantum dot, said different quantum dot, said fluorescent protein and said fluorescent molecule, as a result of said enzyme reactions to measure said activity of said enzymes.

20. The method of claim 19 wherein said enzymes are selected from the group consisting of nuclease, nucleic acid-modifying enzyme, nucleic acid-synthesizing enzyme, protease, protein-modifying enzyme, poly saccharide-degrading enzyme, saccharide-nucleotide-synthesizing enzyme, and glycosyltransferase.

21. An activity measurement molecule comprising a biomolecule bonded to a quantum dot via a biotin-avidin bond and covalently bonded to a fluorescent protein, wherein said biomolecule is selected from the group consisting of a nucleic acid, a protein, a peptide, an amino acid, a coenzyme, a saccharide, a poly saccharide, a lipid, derivatives thereof and complexes thereof but excludes double stranded DNA.

* * * * *

SEQUENCE LISTING

<160> NUMBER OF SEQ ID NOS: 8

<210> SEQ ID NO 1
<211> LENGTH: 30
<212> TYPE: DNA
<213> ORGANISM: Artificial
<220> FEATURE:
<223> OTHER INFORMATION: Designed nucleotides

<400> SEQUENCE: 1
agaaccactc ccagcagcag ttacaaactc          30

<210> SEQ ID NO 2
<211> LENGTH: 22
<212> TYPE: DNA
<213> ORGANISM: Artificial
<220> FEATURE:
<223> OTHER INFORMATION: Designed nucleotides

<400> SEQUENCE: 2
actccaattg gcgatggccc tg          22

<210> SEQ ID NO 3
<211> LENGTH: 12
<212> TYPE: PRT
<213> ORGANISM: Artificial
<220> FEATURE:
<223> OTHER INFORMATION: Designed peptide

<400> SEQUENCE: 3

Gln Gly Arg Gly Thr Cys Glu Leu Tyr Lys Gly Gly
1               5                   10

<210> SEQ ID NO 4
<211> LENGTH: 18
<212> TYPE: PRT
<213> ORGANISM: artificial
<220> FEATURE:
<223> OTHER INFORMATION: Designed peptide

<400> SEQUENCE: 4

Gln Gly Arg Gly Thr Cys Glu Leu Tyr Lys Gly Gly His His His His
1               5                   10                  15

His His

```
<210> SEQ ID NO 5
<211> LENGTH: 13
<212> TYPE: PRT
<213> ORGANISM: Artificial
<220> FEATURE:
<223> OTHER INFORMATION: Designed peptide

<400> SEQUENCE: 5

Ser Gly Ile Thr Asp Glu Val Asp Gly Thr Cys Glu Leu
1               5                   10

<210> SEQ ID NO 6
<211> LENGTH: 26
<212> TYPE: PRT
<213> ORGANISM: Artificial
<220> FEATURE:
<223> OTHER INFORMATION: Designed peptide

<400> SEQUENCE: 6

Ser Gly Ser Ser Gly Ile Thr Leu Glu His Asp Gly Thr Cys Glu Leu
1               5                   10                  15

Tyr Lys Gly Gly His His His His His
            20                  25

<210> SEQ ID NO 7
<211> LENGTH: 16
<212> TYPE: PRT
<213> ORGANISM: Artificial
<220> FEATURE:
<223> OTHER INFORMATION: Designed peptide

<400> SEQUENCE: 7

Gly Gly Arg Arg Ser Gly Thr Cys Gly Gly His His His His His
1               5                   10                  15

<210> SEQ ID NO 8
<211> LENGTH: 18
<212> TYPE: PRT
<213> ORGANISM: Artificial
<220> FEATURE:
<223> OTHER INFORMATION: Designed peptide

<400> SEQUENCE: 8

Ser Gly Thr Asp Glu Val Asp Gly Thr Cys Gly Gly His His His
1               5                   10                  15

His His
```